(12) United States Patent
Han et al.

(10) Patent No.: US 8,771,933 B2
(45) Date of Patent: Jul. 8, 2014

(54) CONTINUOUS-FLOW DEFORMABILITY-BASED CELL SEPARATION

(75) Inventors: Jongyoon Han, Bedford, MA (US); Hansen Bow, Rolling Hills Estates, CA (US); Patrick Abgrall, Toulouse (FR)

(73) Assignee: Massachusetts Institute of Technology, Cambridge, MA (US)

( * ) Notice: Subject to any disclaimer, the term of this patent is extended or adjusted under 35 U.S.C. 154(b) by 282 days.

(21) Appl. No.: 12/899,197

(22) Filed: Oct. 6, 2010

(65) Prior Publication Data

US 2011/0081674 A1    Apr. 7, 2011

Related U.S. Application Data

(60) Provisional application No. 61/249,167, filed on Oct. 6, 2009.

(51) Int. Cl.
*A01N 1/02* (2006.01)

(52) U.S. Cl.
USPC .............. 435/2; 435/29; 435/173.9; 435/325; 977/840

(58) Field of Classification Search
None
See application file for complete search history.

(56) References Cited

U.S. PATENT DOCUMENTS

2006/0246575 A1* 11/2006 Lancaster et al. .......... 435/287.2
2007/0090026 A1*  4/2007 Han et al. ........................ 209/2

OTHER PUBLICATIONS

Chen X. et al., "Continuous flow microfluidic device for cell separation, cell lysis and DNA purification", Analytica Chimica Acta, 2007(published online Nov. 30, 2006), vol. 584, pp. 237-243; with Supplemental Data pp. 1-6.*
Davis J.A. et al., "Deterministic hydrodynamics: Taking blood apart", PNAS, Oct. 3, 2006, vol. 103, No. 40, pp. 14779-14784.*
Hu X. et al., "Marker-specific sorting of rare cells using dielectrophoresis", PNAS, Nov. 1, 2005, vol. 102, No. 44, pp. 15757-15761.*
Pamme N., "Continuous flow separations in microfluidic devices", Lab Chip., 2007, vol. 7, pp. 1644-1659.*

* cited by examiner

*Primary Examiner* — Satyendra Singh
(74) *Attorney, Agent, or Firm* — Gesmer Updegrove LLP

(57) ABSTRACT

This invention provides methods utilizing a microfluidic device that can quickly and accurately discern differences in deformability between individual cells and sets of cells and continuously fractionate populations of cells based on their deformability. This information may be important in disease diagnosis and treatment efficacy monitoring. For example such a device may be able to determine the stage of malarial infection by using red blood cell deformability. Additionally, methods of the invention may be used as a tool to screen drugs that can make cells more flexible in diseases such as sickle cell anemia that causes sickle cell crises. The relatively low manufacturing and operation costs of methods of the invention enable this device to be used in resource-limited settings to diagnose and monitor disease.

39 Claims, 7 Drawing Sheets

C

CONTINUOUS-FLOW DEFORMABILITY-BASED CELL SEPARATION

CROSS REFERENCE TO RELATED APPLICATIONS

This application claims the benefit of U.S. Ser. No. 61/249,167, filed on 6 Oct. 2009 which is incorporated in its entirety herein by reference.

BACKGROUND OF THE INVENTION

Change in cell stiffness is a characteristic of several hematological diseases. Examples of such diseases may involve red blood cells (e.g. malaria and sickle cell anemia), white blood cells (leukemia and leukostasis), and metastatic solid-organ tumor cells (circulating tumor cells and the more extreme carcinocythemia). Often, increases in blood cell stiffness lead to loss of the cells' ability to squeeze through capillaries, resulting in organ failure, coma, and ultimately death.

SUMMARY OF THE INVENTION

In one embodiment, this invention provides a method of sorting a fluid mixture comprising a plurality of cells, said method comprising the steps of:
i. loading a fluid mixture comprising a plurality of cells in a cell sorter comprising:
   a first substrate comprising plurality of parallel trenches, arranged at intervals, the trenches each have a contour of a pair of walls and a bottom.
   a second substrate positioned parallel to said first substrate, such that a spacing is formed between said first and said second substrates;
   a sample inlet to said sorter;
   a sample outlet from said sorter;
ii. applying a force field at a non-zero angle with respect to the length of said trenches, whereby applying said force field allows for separation of said plurality of cells; and
iii. collecting separated cells obtained in (b) from said sample outlet.

In one embodiment, the separation is a result of the difference in cell deformability of different cells in said plurality of cells. In one embodiment, the separation is a result of the difference in cell stiffness of different cells in said plurality of cells. In one embodiment, the method is used for disease diagnosis and/or for treatment efficacy monitoring. In one embodiment, the method is used as a tool for drug screening. In one embodiment, the method is used for isolation of a sub-population of cells. In one embodiment, the cells are cancer cells.

In one embodiment, the cell separation rate is less than 0.1 seconds per cell. In one embodiment, the cell separation rate ranges between 0.1-1 seconds per cell. In one embodiment, the method reduces or eliminates clogging of said sorter. In one embodiment, the force field at a non-zero angle with respect to the length of said trenches is an electrostatic force field. In one embodiment, the electrostatic force field provides an electroosmotic driving force for said fluid. In one embodiment, the force field is a pressure-driven fluid flow. In one embodiment, the fluid has an ionic strength of about 1-1000 mM.

In one embodiment, the sorting is deformability-based. In one embodiment, the sorting is size-based. In one embodiment, the sorting is charge-based. In one embodiment, the depth of said trenches ranges between 10-100,000 nm. In one embodiment, the spacing between said second substrate and said first substrate ranges between 10-50,000 nm. In one embodiment, the width of said trenches ranges between 10-1,000,000 nm. In one embodiment, the length of said trenches ranges between 10 nm and 10 cm. In one embodiment, the sample inlet, the sample outlet or a combination thereof are in fluid communication with a reservoir. In one embodiment, voltage is applied to the reservoir. In one embodiment, the applied voltage is less than 1000 V. In one embodiment, pressure is applied to the reservoir. In one embodiment, the fluid mixture comprises a cell mixture. In one embodiment, the fluid mixture comprises a buffered solution. In one embodiment, the method further comprising the step of sorting a sample of said fluid mixture two or more times, wherein the pH or ionic strength of said buffered solution is varied at the time of said sorting.

In one embodiment, the trenches comprise a material having a Young's Modulus of at least 500 kPa. In one embodiment, the ratio between the length of said trenches and the spacing between the first and second substrates is at least 3:1. In one embodiment, the ratio between the length of said trenches and the spacing between the first and second substrates ranges between 10:1 and 100:1.

In one embodiment, the spacing between the second substrate and the first substrate is less than 50% of the spacing between the second substrate and the bottom of the trenches of the first substrate. In one embodiment, the spacing between the second substrate and the first substrate ranges between 10% and 70% of the spacing between the second substrate and the bottom of the trenches of the first substrate. In one embodiment, spacing between the first and the second substrate ranges between 0.1-10 μm. In one embodiment, the sorter conducts fluid, when fluid is introduced in said sorter. In one embodiment, the sorter employs a force field for conducting the fluid through the sorter. In one embodiment, the direction of the force field is diagonally to the length of the trenches. In one embodiment, the direction of the force field is at a non-zero angle and at an angle that is less than 90 degrees with respect to the length of the trenches. In one embodiment, the force field is a fluid flow. In one embodiment, the force field is an electric field. In one embodiment, the sample inlet comprises sample loading ports. In one embodiment, the sample outlet comprises sample collection ports.

In one embodiment, the first substrate, the second substrate, portions thereof or a combination thereof comprises PDMS, NOA 81, glass, silicon, $SiO_2$ or a combination thereof. In one embodiment, the first substrate, the second substrate, portions thereof or a combination thereof comprises a transparent material. In one embodiment, the surface of the first substrate, the second substrate, portions thereof or a combination thereof are coated to reduce cell adhesion. In one embodiment, the sorter is part of a microchip. In one embodiment, the microchip is disposable.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

First, a 2-level negative PDMS stamp was made using soft lithography techniques from a silicon template. A drop of UV-sensitive prepolymer (NOA 81, Norland Optical Adhesives, USA) was stamped on a glass slide (as backing material) and exposed to UV. Similarly, a drop of NOA was stamped using a flat PDMS slab and exposed to UV on a PDMS backing, which was then treated with oxygen plasma to improve adhesion. After peeling off the stamps, the two pieces were brought in contact and bonded by completing the crosslinking with a second exposure to UV. This method of fabrication results in devices that are more rigid than devices with fluid channels made of only PDMS.

Figure 1:
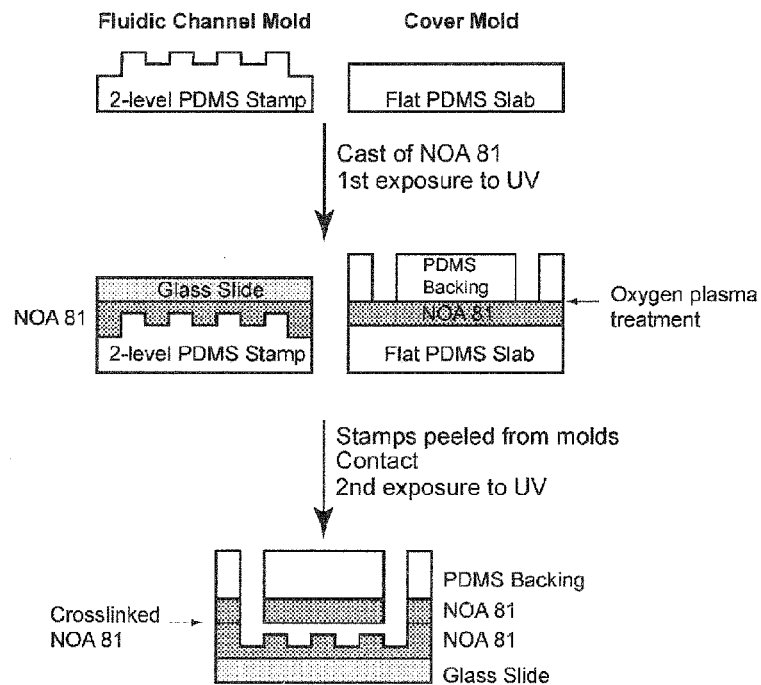
FIG. 1 illustrates an embodiment of fabrication details of polyurethane (NOA 81) devices cast from PDMS molds.
Figure 2:
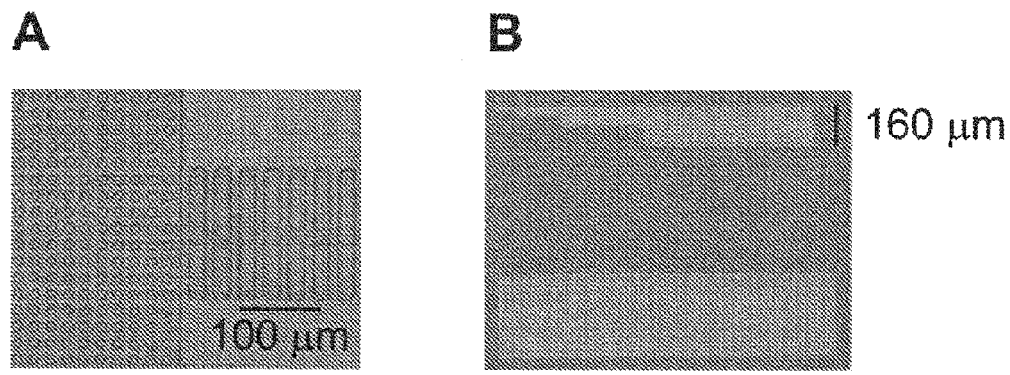
Figure 2:
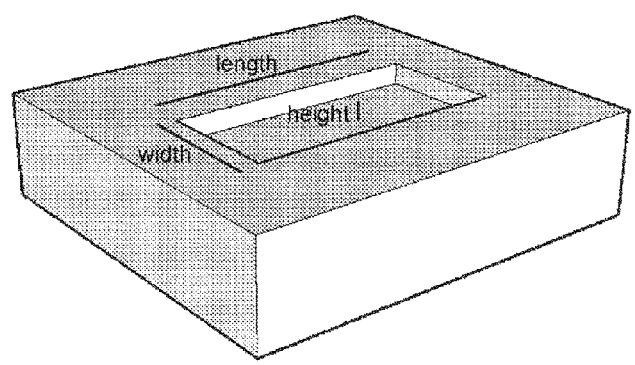

FIG. 2A demonstrates an embodiment of a device; A. Picture from top of actual device near entrance. Pillars at the entrance act as a filter to prevent objects larger than the expected size from entering the critical region of device operation. B. Test structures indicating 2 um deep features with aspect ratio of up to 320/2 did not collapse. Newton's rings can be seen in the 320 um wide rectangle indicating the absence of the two substrates touching. C. In the context of this disclosure the "aspect ratio" is defined as the width/height, where width<length and the top of the pictured structure is covered by a second substrate. In another embodiment, the width described above corresponds to the length of the trenches as described in other embodiments of the invention, or the length of trenches of two sorting units, placed adjacent to each other. In one embodiment, the two sorting units share the same set of supporting structures or pillars, holding the second substrate suspended over the first, in the central region between the two sorting units. In one embodiment, the height in this figure corresponds to the depth of the trenches. In another embodiment, the height in the figure corresponds to the depth of the trenches plus the height of the supporting pillars, i.e. the dimension of the side structures of NOA 81 as shown on the bottom of FIG. 1.

Figure 3:
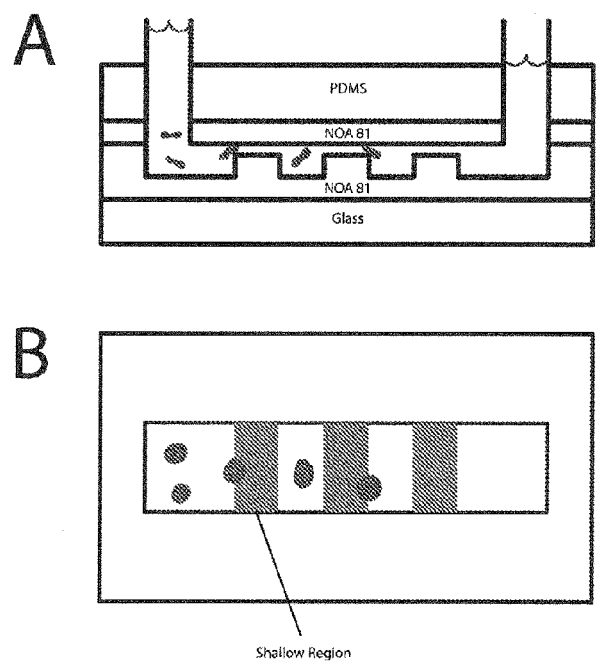

FIG. 3 demonstrates an embodiment of the separation principle; A. Side-view of device with slits in series. The height of red blood cells is greater than the heights of the slits. Therefore, the cells must deform to get through; B. Top-view of the device. The height of the slits corresponds to the spacing between the first and the second substrates in the region of the trenches and/or in the region surrounding each trench as described in other embodiments. In one embodiment, slits are the thin regions or the shallow regions of the device as described in other embodiments.

Figure 4:
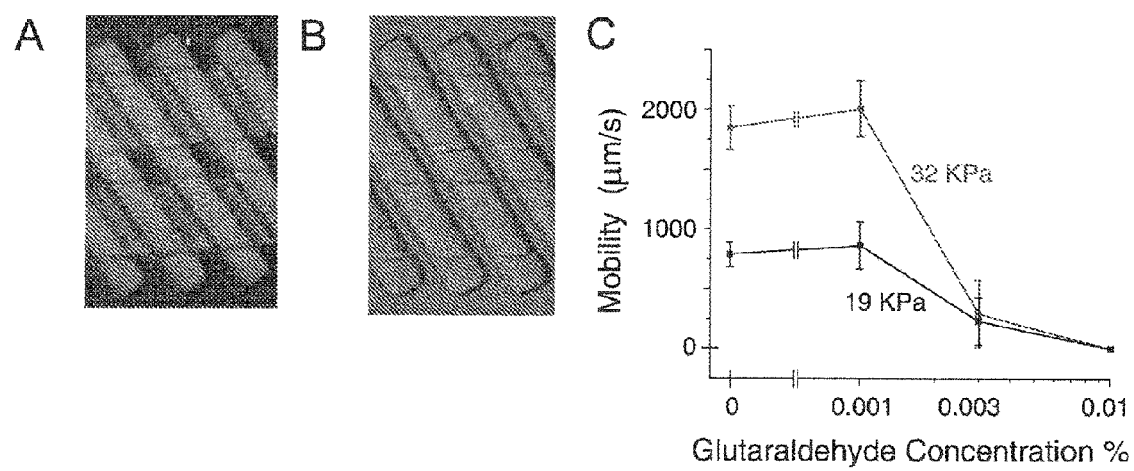
Figure 5:
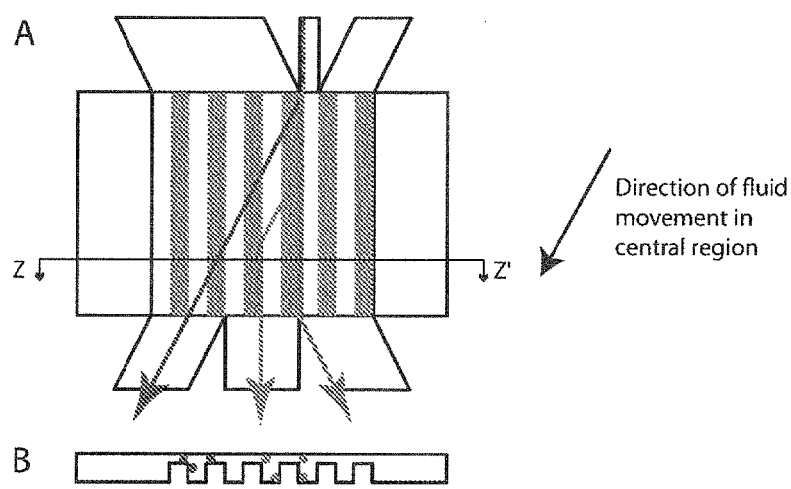

FIG. 4 illustrates embodiments of: A. red blood cells (RBCs) aligned at the entrance of a 1 μm slit under a pressure difference of 40 kPa. The surface area of red blood cells does not expand significantly (typically less than 10% before it rips). Because the surface-area to volume ratio of RBCs is constrained, they are unable to pass through slits less than a certain gap width apart. B. RBCs treated with 0.1% Glutaraldehyde (GA) maintain their biconcave structure at the entrance of 2 μm slits under a pressure difference of 40 kPa. Glutaraldehyde cross-links proteins in the membrane and in the cytosol of RBCs, making them stiffer. The RBCs pictured here do not deform much, and hence are unable to pass through 2 μm slits. C. Mobility vs. GA concentration. Higher GA concentration results in increased cell stiffness, resulting in decreased mobility for a given ambient fluid velocity. The slit gap is the vertical gap that defines the spacing between the two substrates at the trenches area. These are the shallow regions of a unit of the sorter. FIG. 5 illustrates embodiments of a device. 5A. Top view of continuous-flow deformability-based separation device; the red line (arrow pointing from top to bottom left) indicates the trajectory more deformable cells will take, as they are not hindered by the shallow regions. The blue line (arrow pointing to bottom right, showing vertical movement of cells from top to bottom) indicates the trajectory of rigid cells, which slide parallel to the constriction posed by the slit. 5B. Side-view of cross-section Z-Z' showing three groups of separated cells.

Figure 6:
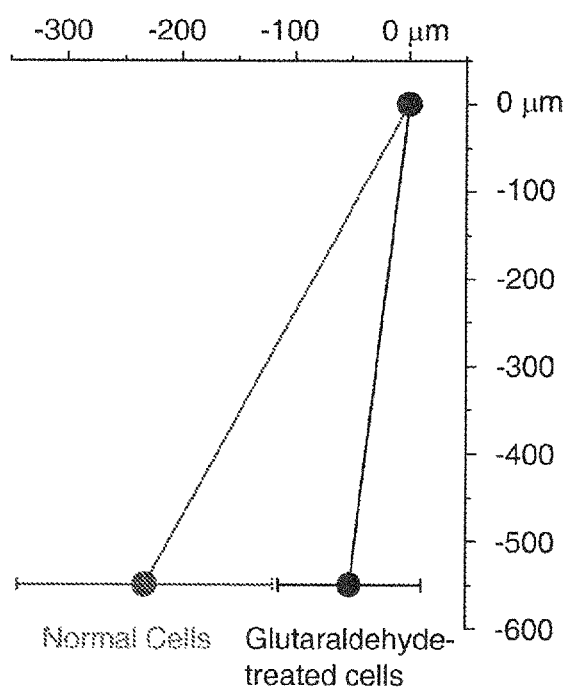

FIG. 6 is a plot of Mean and standard deviations of cell locations as they pass 550 μm distance in a sorter unit(s). Glutaraldehyde-treated cells were immersed in a 0.003% solution of Glutaraldehyde in PBS for 30 minutes before being washed with PBS 3 times. Experiments were performed separately using two identical devices and the same pressures on respective reservoirs.

Figure 7:
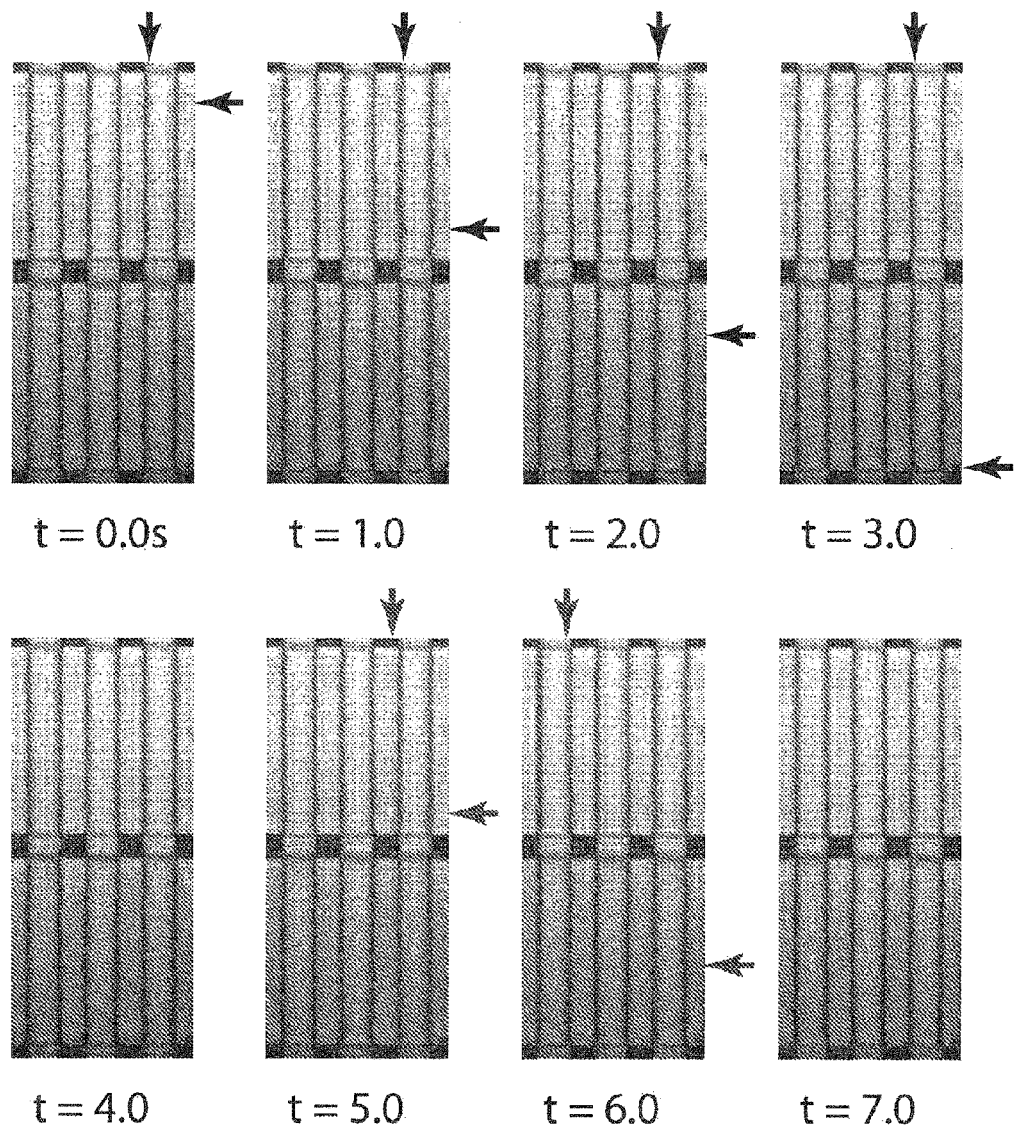

FIG. 7 is an image showing two red blood cells deflected at different angles. From times 0.0 to 3.0 s, the first red blood cells slides along the slit entrance. From 5.0 to 6.0 s, the second red blood cell is able to enter the slit and travels at a different angle than the first red blood cell. Operating pressures in each of the reservoirs were maintained constant throughout these frames. Presumably the second red blood cell is more deformable than the first.

Figure 8:
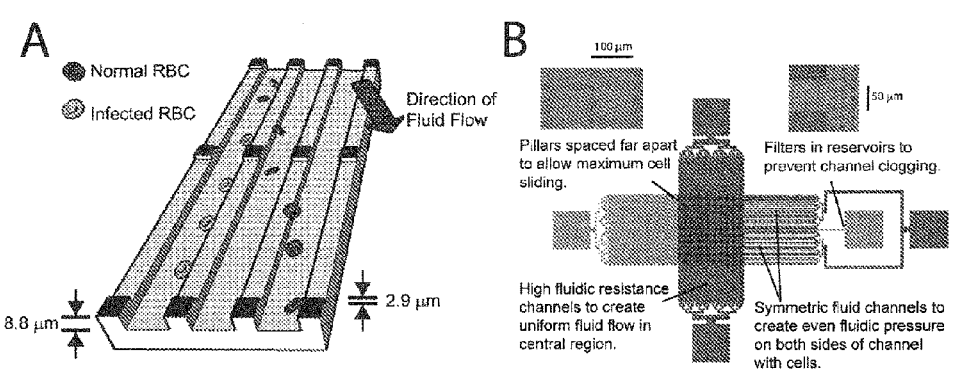

FIG. 8 is an illustration of a device; A. Illustration of device structure and operation. Fluid flows diagonally with respect to the slits. Infected RBCs (gray) slide along the edge of a slit, while normal RBCs (Black) follow the direction of fluid flow. The distance between the second substrate (cover) and the top of the trenches is 2.9 μm. The distance between the black pillars along a slit is 100 μm (shown more clearly in part B). Accordingly, the aspect ratio of this device is 100 μm/2.9 μm=34.5 B. Details regarding device architecture. All ports have pillars spaced 10 μm apart to filter out particles that are outside the size-range of interest (e.g. dust, white blood cells, coagulated platelets). The fluidic resistance of the channels is substantially larger in the channels leading to the central region to ensure uniform fluid flow in the center region.

Figure 9:
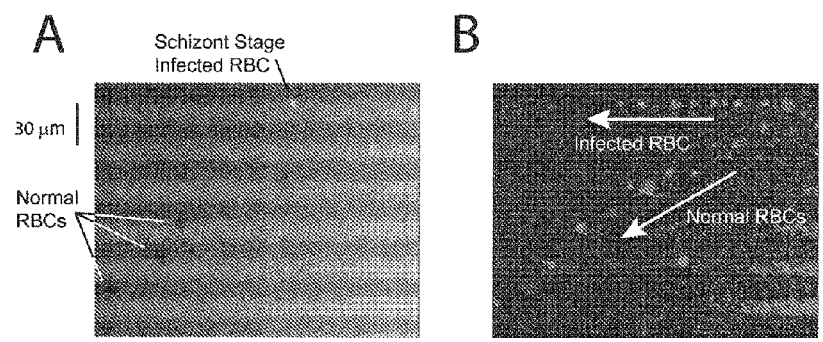

FIG. 9 demonstrates frames from a movie; 9A) Still frame from movie. Malaria infected RBC's stained with Hoechst dye, fluoresce under UV illumination, while uninfected cells appear as shadows. 9B) Superimposed and merged images of same movie. The infected cell can be seen moving horizontally, while the normal cells move diagonally.

Figure 10:
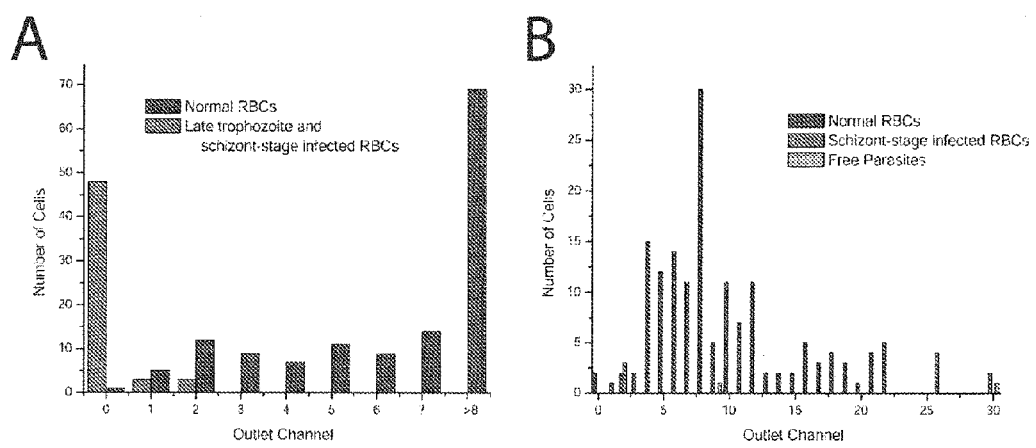

FIG. 10 shows histograms of embodiments of a separation method; 10A. Histogram showing separation between enriched infected RBCs and normal RBCs. 10B. Demonstration of device selectivity. The device was able to isolate 4 schizont-stage infected RBCs from a population of 164 cells.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment of this invention, there is provided a unique continuous-flow separation of cells such as red blood cells (e.g. malaria and sickle cell anemia), white blood cells (leukemia and leukostasis), and metastatic solid-organ tumor cells (circulating tumor cells and the more extreme carcinocythemia), in a microfabricated chip. The separation is based on differential bidirectional transport of cells of different deformability through periodic arrays of microfabricated nanofilters or slits, which in one embodiment, comprises the use of a microfabricated cell sieving chip or sorter that can fractionate cells with separation efficiency comparable or higher than current means of cell separations.

In one embodiment, this invention provides a method of sorting a fluid mixture comprising a plurality of cells, said method comprising the steps of:
i. loading a fluid mixture comprising a plurality of cells in a cell sorter comprising:
  a first substrate comprising plurality of parallel trenches, arranged at intervals, the trenches each have a contour of a pair of walls and a bottom.
  a second substrate positioned parallel to said first substrate, such that a spacing is formed between said first and said second substrates;
  a sample inlet to said sorter;
  a sample outlet from said sorter;
ii. applying a force field at a non-zero angle with respect to the length of said trenches, whereby applying said force field allows for separation of said plurality of cells; and
iii. collecting separated cells obtained in (b) from said sample outlet.

In one embodiment, the separation is a result of the difference in cell deformability of different cells in the plurality of cells. In one embodiment, the separation is a result of the difference in cell stiffness of different cells in the plurality of cells. In one embodiment, the method is used for disease diagnosis and/or for treatment efficacy monitoring. In one embodiment, the method is used as a tool for drug screening. In one embodiment, the method is used for isolation of a sub-population of cells. In one embodiment, the cells are cancer cells. In one embodiment, the method is used for disease treatment or for condition treatment.

In one embodiment, the cell separation rate is less than 0.1 seconds per cell. In one embodiment, the cell separation rate ranges between 0.1-1 seconds per cell. In one embodiment, the method reduces or eliminates clogging of said sorter. In one embodiment, the force field at a non-zero angle with respect to the length of said trenches is an electrostatic force field. In one embodiment, the electrostatic force field provides an electroosmotic driving force for said fluid. In one embodiment, the fluid flow is a pressure-driven fluid flow. In one embodiment, the fluid has an ionic strength of about 1-1000 mM.

In one embodiment, the sorting is deformability-based. In one embodiment, the sorting is size-based. In one embodiment, the sorting is charge-based. In one embodiment, the depth of said trenches ranges between 10-100,000 nm. In one embodiment, the spacing between said second substrate and said first substrate ranges between 10-50,000 nm. In one embodiment, the width of said trenches ranges between 10-100,000 nm. In one embodiment, the length of said trenches ranges between 10 nm and 10 cm. In one embodiment, the sample inlet, the sample outlet or a combination thereof are in fluid communication with a reservoir. In one embodiment, voltage is applied to the reservoir. In one embodiment, the applied voltage is less than 1000 V. In one embodiment, pressure is applied to the reservoir. In one embodiment, the fluid mixture comprises a cell mixture. In one embodiment, the fluid mixture comprises a buffered solution. In one embodiment, the method further comprises the step of sorting a sample of said fluid mixture two or more times, wherein the pH or ionic strength of said buffered solution is varied at the time of said sorting.

In one embodiment, the trenches comprise a material having a Young's Modulus of at least 500 kPa. In one embodiment, the ratio between the length of said trenches and the spacing between the first and second substrates in the trenches region is at least 3:1. In one embodiment, the ratio between the length of said trenches and the spacing between the first and second substrates ranges between 10:1 and 100:1.

In one embodiment, the spacing between the second substrate and the first substrate in the trenches region is less than 50% of the spacing between the second substrate and the bottom of the trenches of the first substrate. In one embodiment, the spacing between said second substrate and the first substrate ranges between 10% and 70% of the spacing between the second substrate and the bottom of the trenches of the first substrate. In one embodiment, spacing between the first and the second substrate ranges between 0.1-10 μm. In one embodiment, 1 μm is 1 micrometer. In one embodiment, the sorter conducts fluid, when fluid is introduced in said sorter. In one embodiment, the sorter employs a force field for conducting the fluid through the sorter. In one embodiment, the direction of said force field is diagonally to the length of said trenches. In one embodiment, the direction of said force field is at a non-zero angle and at an angle that is less than 90 degrees with respect to the length of said trenches. In one embodiment, the force field is a fluid flow. In one embodiment, the force field is an electric field. In one embodiment, the sample inlet comprises sample loading ports. In one embodiment, the sample outlet comprises sample collection ports.

In one embodiment, the first substrate, the second substrate, portions thereof or a combination thereof comprises PDMS, NOA 81, glass, silicon, $SiO_2$ or a combination thereof. In one embodiment, the first substrate, the second substrate, portions thereof or a combination thereof comprises a transparent material. In one embodiment, the surface of the first substrate, the second substrate, portions thereof or a combination thereof are coated to reduce cell adhesion. In one embodiment, the sorter is part of a microchip. In one embodiment, the microchip is disposable.

1. Definitions:

In one embodiment, a cell is a biological cell. In one embodiment, deformability is the ability of a cell to change its shape or its geometry. In one embodiment, deformability is a measure of the flexibility of a cell. In one embodiment, deformability is the ability of a cell to deform. In one embodiment, deformability is the ability of a cell to squeeze through a narrow gap. In one embodiment, deformability is a cell property that varies in different cell types. In one embodiment, deformability is a cell property that varies in cells that were modified biologically or chemically. In one embodiment, deformability is reduced by increasing stiffness of the cell.

In one embodiment, fluid mixture is a mixture of species in a liquid. In one embodiment, a fluid mixture is a fluid containing a cell mixture. In one embodiment cell mixture is a mixture in which cells with different properties are present. In one embodiment the fluid is a solution.

In one embodiment, a trench is a channel in or a cut through the substrate surface. In one embodiment, the trench is defined by its length, width and depth.

In one embodiment, force field is a field that forces liquid or fluid through the device. In one embodiment, force field is a field that allows conductance of fluid or fluid mixture through the device in one embodiment, force field is any force that causes an object to displace from its original location.

The field may be the ambient velocity of the fluid, a magnetic field, or an electric field, gravity, or light.

In one embodiment, treatment efficacy monitoring means that cell sorting by devices and methods of this invention gives indication as to the efficiency of a certain treatment. In one embodiment, the treatment affects the deformability of the cells involved.

In one embodiment, cell separation rate is defined by the number of cells that enter the separation region of the sorter per unit time. Rates range from 1 cell/sec to 10,000 cells/sec and higher values can be obtained if the device is operated in parallel with identical devices. In one embodiment, ionic strength is a measure of the concentration of ions in a solution. In one embodiment, ionic strength depends on the concentration of the ions and on their charges. In one embodiment, a cell mixture is a mixture comprising various cells. In some embodiments the cell mixture comprises different cell types. In one embodiment, the mixture comprises cells of the same type that differ in their properties. In some embodiments some cells in a mixture were treated and others were not. In some embodiments, some cells in a mixture are modified and others are not. In some embodiments, some cells are healthy and others are not.

In one embodiment, Young's modulus (E) is a measure of the stiffness of an isotropic elastic material. In one embodiment, Young's modulus is the modulus of elasticity, or the elastic modulus or the tensile modulus. In one embodiment, Young's modulus is defined as the ratio of the uniaxial stress over the uniaxial strain. In one embodiment, Young's modulus is experimentally determined from the slope of a stress-strain curve created during tensile tests conducted on a sample of the material. Young's modulus is the ratio of stress, which has units of pressure, to strain, which is dimensionless; therefore Young's modulus has units of pressure.

The SI unit of modulus of elasticity (E, or less commonly Y) is the pascal (Pa or $N/m^2$); the practical units are megapascals (MPa or $N/mm^2$) or gigapascals (GPa or $kN/mm^2$). In one embodiment, Young's modulus is expressed as pounds per square inch (psi).

In one embodiment, a microfluidic device is a device comprising features with dimensions in the micron scale. In one embodiment, a microfluidic device is referred to or is part of a "microchip". In one embodiment, the microchip is part of the microfluidic device. In one embodiment, a microchip is a device constructed on, constructed in or is part of at least one substrate. Such microchip comprises features with dimensions in the micrometer range. In one embodiment, a microfluidic device is a device comprising features with at least one dimension between 1 micrometer (1 µm) and 1000 micrometer (1000 µm). In one embodiment, a microfluidic device comprises trenches and/or channels with width or depth in the micron scale and with length in the micron, millimeter or centimeter scale. In one embodiment, such trenches or channels are referred to as microchannels. In one embodiment, liquid can be made to pass through the trenches or microchannels. In one embodiment, a microfluidic device is a device through which fluid can be made to pass. In one embodiment, fluid can be a liquid. In one embodiment, the liquid can be pure. In one embodiment, the liquid can be a mixture. In one embodiment, the liquid can be a solution. In one embodiment, the solution can contain molecules or ions and/or cells. In one embodiment, the solution can be aqueous or organic. In one embodiment, an aqueous solution containing ions can be a salt solution.

In one embodiment, the liquid comprises charged species. In one embodiment, charged means electrically charged. In one embodiment, charged species is a species that can be influenced by an electric field. In one embodiment, a charged species can be made to migrate in an electric field. In one embodiment, a charged species is attracted to a region with an opposite charge. In one embodiment, charged species migrate toward a region or a pole with an opposite charge, and are repelled or migrate away from regions with the same charge. In one embodiment, the charged species is a molecule, an ion, a particle, a cluster, a cell or an aggregate carrying an extra charge. In one embodiment, charged species is a species that is not electrically neutral. In one embodiment, the charged species is a peptide, a protein, a c nucleotide, a DNA or RNA segment, a nanoparticle, a microparticle, a bead or a biological cell. In one embodiment, the cell is a red blood cell. In one embodiment, the cell is a white cell. In one embodiment, the cell is a cancer cell. In one embodiment, the charged species is a biomolecule.

In one embodiment, a substrate is the supporting structure of a microfluidic device. In one embodiment, the substrate is the material on which or in which the microfluidic device is built. In one embodiment, the substrate is a piece of material from which the device or portions of it will be made. In one embodiment, the substrate or the device is comprised of a transparent material. In one embodiment, the transparent material is pyrex, silicon dioxide, silicon nitride, quartz or SU-8, or a thiolene-based polymer. In one embodiment, the device is coated with a low-autofluorescent material. In one embodiment, the substrate, the device or portions of the device are made of silicon. In one embodiment, the substrate, the device or portions of the device are made of a polymer. In one embodiment, the polymer is PDMS. In one embodiment, the polymer is a thiolene based UV-adhesive. In one embodiment, the UV adhesive is Norland Optical Adhesive NOA 81 with a Young's Modulus of 1.4 GPa. In one embodiment, such polymer is transparent and offers better resistance to solvents than PDMS. In one embodiment, the polymer is chosen from the UV curable Norland adhesives NOA 60, NOA 61, NOA 63, NOA 65, NOA 68, NOA 71, NOA 73, NOA 81, NOA 88 and UVS 91, the UV/heat-curable adhesives NOA 83H, NBA 121 and NBA 123, the UV/vis-curable adhesives NOA 72, and the heat-curable adhesive NBA 155. In one embodiment, the polymer is Polyuretane, poly methyl methacrylate, imprinted plastic, or polymers included in or related to the polyurethane or to the methyl methacrylate polymer families.

In one embodiment, a reservoir is any container that can hold liquids. In one embodiment, a reservoir is a vessel. In one embodiment, the reservoir has a channel structure. In one embodiment, any reservoir of the invention any channel is rounded. In one embodiment, the reservoir is filled with buffer. In one embodiment, the buffer-filled reservoir is grounded using one electrode. In one embodiment, any voltage can be applied to the buffer-filled reservoir or to any reservoir of the invention using one or more electrodes.

In one embodiment, an electric field is the space surrounding an electric charge. In one embodiment, the electric field exerts a force on other electrically charged objects. In one embodiment, a stationary charged particle in an electric field experiences a force proportional to its charge. In one embodiment, an electric field can be induced by applying a voltage. In one embodiment, an electric field can be induced in the area between two electrodes to which an unequal voltage is applied. In one embodiment, certain distribution of positive or negative charges in space can give rise to an electric field.

In one embodiment, electroosmotic flow or electro-osmotic flow, often abbreviated EOF is the motion of ions in a solvent environment through very narrow channels, where an applied voltage across the channels causes the ion migration.

In one embodiment, a "ground", "grounded" or "electrically grounded" are terms used to describe the relative voltage applied to one side of a microchannel, or the relative voltage applied to regions or to electrodes used in methods of this invention. In one embodiment, ground is the reference point in an electrical circuit from which other voltages are measured, a common return path for electric current (earth return or ground return), or a direct physical connection to the Earth. For measurement purposes, the earth or ground serves as a constant potential reference against which other potentials can be measured. In one embodiment, an electrical ground system serves as an adequate zero-voltage reference level.

In one embodiment, an external gate voltage is a voltage applied external to microchannels, trenches or reservoirs of the invention, and not directly to the liquid carrying the charged species. In one embodiment, "gate" means that the application of such voltage can gate the liquid flow, by causing ions to move or to stop moving in a certain direction. In one embodiment, "gate" or "gating" means switching the direction of the flow, or switching the direction of migrating ions. In one embodiment, gating can stop flow. In one embodiment, gate voltage influences charged species by inducing an electric field. The electric field induced by the gate voltage may cause the accumulation, migration, depletion or a combination thereof of the charged species in or away from defined areas in the microfluidic channels. In one embodiment, gate voltages may help cell separation or make the cell separation more efficient or results in higher resolution of cell separation.

In one embodiment, devices used in methods of this invention are made by lithography and etching processes and/or stamping processes. In one embodiment lithography and etching processes are the conventional processes used in the semiconductor fabrication industry. In one embodiment, processes used to make devices of this invention comprise printing, contact printing, deposition, use of sacrificial layers, sputtering and any other processes known to a person skilled in the art.

In some embodiments, the devices of this invention comprise a conduit connecting between microchannels and/or between microchannels or trenches of the device and the device or sorter's inlet and outlet. In one embodiment, a conduit connects between the sample inlet and/or the sample outlet and other units related to the device. Other units connected to the device may comprise sample preparation chamber or reservoir or sample preparation container, sample collection container, vessel, syringe or tube. In one embodiment, other units connected to the device may comprise, sample analysis chamber or reservoir or sample analysis container, vessel, syringe or tube. In one embodiment, other units connected to the device may comprise, sample imaging chamber or reservoir or sample imaging container, vessel, syringe or tube. In some embodiments, the term "conduit" may refer to a channel, a connector, a wire, a linkage, a solution-filled capillary, a porous material filled with fluid, a trench, an electrically conducting or semiconducting material. In one embodiment, a conduit is attached directly to the microchannels or directly to the device, or directly to the trenches, or in one embodiment, via an adaptor, a filter, a junction or any other desired material, as will be appreciated by the skilled artisan. In some embodiment, flow is induced in the conduit. In one embodiment, ion flow is permitted through the conduit. It is to be understood that any structuring of the device to accommodate a conduit is what is to be understood as encompassed by the phrase "a conduit linked to the sample inlet, sample outlet or to the device or to the trench region, or to the sorter unit and is part of the present invention.

In one embodiment, the buffer comprises a buffer solution. In one embodiment, a buffer solution is a solution that resists change in hydronium ion ($H^+$) and in hydroxide ion ($OH^-$) concentration. Therefore, a buffer solution resists a pH change. The buffer solution can resist a pH change upon addition of small amounts of acid or base, or upon dilution. Buffer solutions consist of a weak acid and its conjugate base or a weak base and its conjugate acid. In one embodiment, the buffer solution comprises a phosphate buffer. In one embodiment, the buffer solution comprises an acetate buffer, Tris buffer, PIPES or HEPES buffers.

In one embodiment cell sorter is a cell separating device. In one embodiment a solution comprising at least two types of cells may be introduced into the cell sorter, and the different cell types will be separated by the cell sorter. In one embodiment, the cell sorter enables to bring apart, to divide between and/or to sort various cells based on the difference in their properties. In one embodiment, the cell sorter is a device to sort cells. In one embodiment, the cell sorter is a device that separates cells from a cell mixture or from a cell solution comprising more than one type of cells. In one embodiment, a sorter unit is any unit within the cell sorter comprising at least one trench, at least one trench with one or two thin regions on the trench sides. In one embodiment, a sorter unit is a series of neighboring trenches (with the thin regions between them). In one embodiment, the sorter unit may be defined with the second substrate and in another embodiment, without the second substrate. In one embodiment, a sorter unit may be defined as a part of the sorter that is defined by the pillars surrounding it, or by the four pillars on the corners of any such unit. In one embodiment the sorter is referred to as a microseparator.

2. Devices of this Invention

In one embodiment, the substrates and/or other components of the sorter can be made from a wide variety of materials including, but not limited to, silicon, silicon dioxide, silicon nitride, glass and fused silica, gallium arsenide, indium phosphide, III-V materials, PDMS, silicone rubber, aluminum, ceramics, polyimide, quartz, plastics, resins and polymers including polymethylmethacrylate, polyurethanes (PUR/PU), acrylics, polyethylene, polyethylene tereptphalate, polycarbonate, polystyrene and other styrene copolymers, polypropylene, polytetrafluoroethylene, superalloys, zircaloy, steel, gold, silver, copper, tungsten, molybdeumn, tantalum, KOVAR, KEVLAR, KAPTON, MYLAR, teflon, brass, sapphire, etc., or a combination thereof. High quality glasses such as high melting borosilicate or fused silica may be used, in some embodiments, for their UV transmission properties when any of the sample manipulation and/or detection steps require light based technologies. In some embodiments the construction material for the cell sorter is chosen for its robustness, for its stability, such that it will not collapse, or for its fluid conduction compatibility. In one embodiment, the material is chosen for the ease and low cost preparation scheme that is possible using such material. In addition, as outlined herein, portions of the internal and/or external surfaces of the device may be coated with a variety of coatings as needed, to facilitate manipulation or for the separation and/or detection technique performed. In one embodiment, the polymer is a thiolene based UV-adhesive. In one embodiment, the UV adhesive is Norland Optical Adhesive NOA 81 with a Young's Modulus of 1.4 GPa. In one embodiment, such polymer is transparent and offers better resistance to solvents than PDMS. In one embodiment, the polymer is chosen from the UV curable Norland adhesives NOA 60, NOA 61, NOA 63, NOA 65, NOA 68, NOA 71, NOA 73, NOA 81, NOA 88 and UVS 91, the UV/heat-curable adhesives NOA 83H, NBA 121 and NBA 123, the UV/vis-curable adhesives NOA 72, and the heat-curable adhesive NBA 155. In one embodiment, the polymer is Polyuretane, poly methyl methacrylate, imprinted plastic or polymers included by or related in structure to Polyuretane, poly methyl methacrylate or thiolene-based polymers.

In one embodiment, pillars are used to hold the second substrate over the first substrate. In one embodiment, the pillars height measured vertically from the top of the trenches defines the spacing between the first and the second substrate. In one embodiment, the pillars comprise the same materials as the substrate, or in another embodiment, are comprised of a suitable material which prevents adhesion to the pillars. In one embodiment, the pillars are supporting structures. In one embodiment, pillar position defines the borders of one sorter unit. In one embodiment, one pillar supports two or four minimal sorter units placed in parallel or placed in conjunction with each other. In one embodiment, four pillars define the borders of one sorting unit. In one embodiment, the pillars are the highest level or the highest portion of the first substrate. In one embodiment, pillars height can be measured vertically from the top of the trenches, and in another embodiment, vertically from the bottom of the trenches. When the pillar height is measured from the top of the trenches, the height corresponds to the slit gap size of the thin or shallow regions in the sorter.

In one embodiment, devices used in this invention are described in US 2007/0090026A1, which is incorporated in its entirety herein by reference.

In one embodiment, the invention provides for a microchip comprising the cell sorter or sorters of this invention. In one embodiment, the microchip may be made of a wide variety of materials and can be configured in a large number of ways, as described and exemplified herein in some embodiments, and other embodiments will be apparent to one of skill in the art. The composition of the substrate will depend on a variety of factors, including the techniques used to create the device, the use of the device, the composition of the sample, the cells to be sorted, the type of analysis conducted following cell sorting, the size of internal structures, the presence or absence of electronic components, and the technique used to move fluid, etc. In some embodiments, the devices of the invention will be sterilizable as well, in some embodiments, this is not required. In some embodiments, the devices are disposable or, in another embodiment, re-usable.

Microfluidic chips used in the methods and devices of this invention may be fabricated using a variety of techniques, including, but not limited to, hot embossing, such as described in H. Becker, et al., Sensors and Materials, 11, 297, (1999), hereby incorporated by reference, molding of elastomers, such as described in D. C. Duffy, et. al., Anal. Chem., 70, 4974, (1998), hereby incorporated by reference, injection molding, LIGA, soft lithography, imprint lithography, stamping techniques, silicon fabrication and related thin film processing techniques, as known in the art, photolithography and reactive ion etching techniques, as exemplified herein. In one embodiment, glass etching and diffusion bonding of fused silica substrates may be used to prepare microfluidic chips. In one embodiment, light curing, and especially, UV-light curing is used in methods of fabrication of this invention. In one embodiment, light-induced crosslinking is used for bonding of pieces in the devices. In one embodiment, plasma bonding or plasma treatments are used to bond pieces of the device.

The spacing between the pillars or between the supporting structures in the sorter determines the length of the trenches in one embodiment. For example, as described in FIG. 3B, the length of the two trenches (two white rectangles in the center of the figure) is bordered by supporting structures or pillars. The trenches comprises the deeper regions of the device that form channels for conveying fluid comprising cells to be sorted, as described herein. The shallow regions (three gray rectangles in FIG. 2B) provide steric hindrance such that stiff cells with diameters or with dimensions larger than the shallow region height do not pass readily through these shallow regions. In one embodiment, the pillars or supporting structures are not isolated structures, but rather a continuous structure surrounding the sorter unit. The continuous supporting structure may be a rectangle, a square, or any other continuous closed or semi-closed shape or structure. The height of such supporting structure defines the distance between the second substrate (or outer-most surface thereof) and the bottom of the trenches. The trenches are aligned inside the cavity formed by the supporting structure. The cavity of such supporting structure is subjected to fluid flow in one embodiment. In one embodiment, a cavity or a chamber in the first substrate holds the trenches within it, but the trenches top surface is lower than the surface of the structure surrounding the cavity, such that when a second substrate is placed on the first, the second substrate touches or makes contact with the surrounding structure, but there is a space between the second substrate and the top of the trenches (there is a space between the second substrate and the elevated area between the trenches). Such structure allows for the cells to move freely within and along the trenches and it allows flexible cells to deform while crossing from one trench to another through the narrow slit formed on top of the area between any two trenches. In some embodiments, the second substrate comprises holes, slits or other open areas through which the fluid comprising the cells is injected and through which the fluid comprising the cells is collected. In one embodiment, the second substrate comprises holes, slits or openings to aid in fluid conduction through the sorter. In one embodiment, holes, slits or openings are present between the two substrates or the openings are cutting through portions of the first and/or the second substrate for conveying the fluid comprising the cells through the device. In one embodiment, such openings in the first substrate, the second substrate, the area between the two substrates or a combination thereof comprise or consist of the sorter inlet, the sorter outlet or a combination thereof.

In one embodiment, the microfluidic channels or trenches used in the devices and/or methods of this invention, which convey fluid, may be constructed from a material which renders it transparent or semitransparent, in order to image the solutions being sorted, or in another embodiment, to ascertain the progress of the sorting, etc. In some embodiments, the materials further have high chemical resistance to buffer solutions and/or mild organics. In other embodiments, the material is of a machinable or moldable polymeric material, and may comprise insulators, ceramics, metals or insulator-coated metals. In other embodiments, the channel may be constructed from a polymer material that is resistant to alkaline aqueous solutions and mild organics. In another embodiment, the channels, slits or trenches comprise at least one surface which is transparent or semi-transparent, such that, in one embodiment, imaging of the sorter or the sorter contents is possible.

In one embodiment, the sorter may further comprise microfluidic channels in fluid communication with the sorter. In one embodiment, the latter channels are in fluid communication with a reservoir, or in another embodiment, inlet port, or in another embodiment, outlet port. According to this aspect of the invention, the microfluidic channels may serve as a conduit for conveying material into and out of the sorter.

In one embodiment, a device of this invention may comprise an array comprising one or more sorters. Such arrays may be referred to herein, in other embodiments, as "anisotropic nanofilter arrays (ANAs)". In one embodiment, anisotropy in dimensions means that along a certain axis, the space or vertical gap available for the cells varies. In one embodiment, nanofilter is the slit or thin region. In one embodiment, "nanofilter" can be substituted by a "microfilter" with dimensions in the micrometer range.

In one embodiment, the inlet may comprise an area of the chip in fluidic communication with one or more microfluidic channels, one or more trenches, one or more sorter units in one embodiment, and/or a reservoir, in another embodiment. Inlets and outlets may be fabricated in a wide variety of ways, depending upon, in one embodiment, on the substrate material utilized, and/or in another embodiment, the dimensions used. In one embodiment inlets and/or outlets are formed using conventional tubing, which prevents sample leakage, when fluid is applied to the device, under pressure. In one embodiment inlets and/or outlets are formed of a material which withstands application of voltage, even high voltage, to the device. In one embodiment, the inlet may further comprise a means of applying a constant pressure, to generate pressure-driven flow in the device. In one embodiment, pillars at the inlets act as filters to prevent objects larger than the expected size from entering the critical region of device operation.

The sorters of this invention, may be referred to in some embodiments, as a "device" or "apparatus", and will comprise at least the elements as described herein.

Microfabrication technology, or microtechnology or MEMS, in one embodiment, applies the tools and processes of semiconductor fabrication to the formation of, for example, physical structures. Microfabrication technology allows one, in one embodiment, to precisely design features (e.g., reservoirs, wells, channels) with dimensions in the range of <1 mm to several centimeters on chips made, in other embodiments, of silicon, glass, or plastics. Such technology may be used to construct the sorters, r components of the sorter, or packaging of the sorter, or arrays of sorters, in one embodiment.

In another embodiment, NEMS or nanotechnology is used to construct the sorters or the trenches within the sorter. In one embodiment, the sorter can be fabricated with nanoimprint lithography (NIL), as described in Z. N. Yu, P. Deshpande, W. Wu, J. Wang and S. Y. Chou, Appl. Phys. Lett. 77 (7), 927 (2000); S. Y. Chou, P. R. Krauss, and P. J. Renstrom, Appl. Phys. Lett. 67 (21), 3114 (1995); Stephen Y. Chou, Peter R. Krauss and Preston J. Renstrom, Science 272, 85 (1996) and U.S. Pat. No. 5,772,905 hereby incorporated herein, in their entirety, by reference. In one embodiment, the sorters can be formed by photolithography and reactive ion etching (RIE) techniques, with microfilter gap thickness as thin as 10 nm. In one embodiment, the formation of the device may employ nanoimprint lithography, interference lithography, self-assembled copolymer pattern transfer, spin coating, electron beam lithography, focused ion beam milling, wet-etching, plasma-enhanced chemical vapor deposition, electron beam evaporation, sputter deposition, and combinations thereof. Alternatively, other conventional methods can be used to form the sorters.

In one embodiment, the channels, chambers, and/or filters have dimensions on the order of microns, in the case of the trenches and chambers/reservoirs. In some embodiments, structures with larger dimensions, such as on the order of millimeters, are used, and represent embodiments of this invention. In one embodiment, the width and/or length of the sorters ranges from 100-2000 $\mu$m, and the depth of the microfluidic chamber ranges from 0.1-100 $\mu$m.

In one embodiment, the width of the trenches is between 0.1-1000 $\mu$m, or in another embodiment, between 1 and 150 $\mu$m, or in another embodiment, between 20 and 500 $\mu$m, or in another embodiment, between 25 and 750 $\mu$m, or in another embodiment, between 500 and 1000 $\mu$m or between 1 and 50 $\mu$m. In one embodiment, the width of the trenches is between 1-10 $\mu$m, or in another embodiment, between 10 and 30 $\mu$m, or in another embodiment, between 10 and 50 $\mu$m, or in another embodiment, between 25 and 750 $\mu$m, or in another embodiment, between 0.1 and 100 $\mu$m or between 0.5 and 40 $\mu$m. In one embodiment, the width of the trenches is 15 $\mu$m or 10 $\mu$m. In one embodiment, the width of the trenches ranges between 100 micrometers and 1000 micrometers.

In one embodiment, the depth of the trenches is between 0.1-50 $\mu$m, or in another embodiment, between 0.5 and 5 $\mu$m, or in another embodiment, between 5 and 15 $\mu$m, or in another embodiment, between 10 and 25 $\mu$m, or in another embodiment, between 15 and 50 $\mu$m. In one embodiment, the depth of the trenches is between 0.5-20 $\mu$m, or in another embodiment, between 5 and 15 $\mu$m, or in another embodiment, between 100 and 200 $\mu$m, or in another embodiment, between 1 and 100 $\mu$m, or in another embodiment, between 6 and 14 $\mu$m. In one embodiment, the depth of a trench is the height of a trench's wall. In another embodiment, the depth of a trench is the height of a wall of a trench plus the depth of the thin region.

In one embodiment, the length of the trenches is between 1-1000 $\mu$m or in another embodiment between 50 and 150 $\mu$m, or in another embodiment, between 90 and 110 $\mu$m, or in another embodiment, between 150 and 250 $\mu$m, or in another embodiment, between 10 and 500 $\mu$m. In one embodiment, the length of the trenches is between 10-100 $\mu$m or in another embodiment between 50 and 100 $\mu$m, or in another embodiment, between 100 and 2000 $\mu$m, or in another embodiment, between 100 and 5000 $\mu$m, or in another embodiment, between 50 and 500 $\mu$m. In one embodiment, the length of the trenches is between 100-1000 $\mu$m or in another embodiment between 1000 and 10,000 $\mu$m, or in another embodiment, between 100 and 2000 $\mu$m, or in another embodiment, between 100 and 5000 $\mu$m, or in another embodiment, between 5000 and 10,000 $\mu$m.

In another embodiment, the width of the shallow region is equal to the width of the trenches. In another embodiment, the width of the shallow region is different from the width of the trenches. In one embodiment, the width of the shallow region is between 0.1-1000 $\mu$m, or in another embodiment, between 1 and 150 $\mu$m, or in another embodiment, between 20 and 500 $\mu$m, or in another embodiment, between 25 and 750 $\mu$m, or in another embodiment, between 500 and 1000 $\mu$m or between 1 and 50 $\mu$m. In one embodiment, the width of the shallow region is between 1-10 $\mu$m, or in another embodiment, between 10 and 30 $\mu$m, or in another embodiment, between 10 and 50 $\mu$m, or in another embodiment, between 25 and 750 $\mu$m, or in another embodiment, between 0.1 and 100 $\mu$m or between 0.5 and 40 $\mu$m. In one embodiment, the width of the shallow regions is 15 $\mu$m or 10 $\mu$m.

In another embodiment, the depth of the shallow regions is between 1-10 micrometers, or in another embodiment, between 0.5 and 20 micrometers, or in another embodiment, between 0.1 and 5 micrometers, or in another embodiment, between 1 and 30 micrometers or in another embodiment, between 2 and 6 micrometers. In one embodiment, the depth of the shallow region is 3 micrometers. In another embodiment, the depth of the shallow regions is between 10-50,000 micrometers, or in another embodiment, between 10 and 5000 micrometers, or in another embodiment, between 1 and 1000 micrometers, or in another embodiment, between 1 and 500 micrometers or in another embodiment, between 500 and 5000 micrometers. In one embodiment, the depth of the shallow region is 20 micrometers.

In one embodiment, the length of the shallow region is defined by two adjacent pillars (e.g. black squares in FIG. 8A) bordering the length of a shallow region. In one embodiment, the length of the shallow region is between 1-1000 μm or in another embodiment between 50 and 150 μm, or in another embodiment, between 90 and 110 μm, or in another embodiment, between 150 and 250 μm, or in another embodiment, between 10 and 500 μm. In one embodiment, the length of the shallow region is between 10-100 μm or in another embodiment between 50 and 100 μm, or in another embodiment, between 80 and 2000 μm, or in another embodiment, between 90 and 5000 μm, or in another embodiment, between 50 and 500 μm. In one embodiment, the length of the shallow regions is 100 micrometers. In one embodiment, the length of the shallow region is between 100-2000 μm or in another embodiment between 1000 and 2000 μm.

In one embodiment, the trenches, which form the rows of the device and the shallow regions between the trenches are oriented parallel with respect to each other. In one embodiment, trenches and shallow regions alternately span the device central or core region.

In one embodiment, the sorter of this invention may comprise a plurality of trenches. In one embodiment, the phrase "a plurality of trenches" refers to at least two trenches, or, in another embodiment, more than 5, or, in other embodiments, more than 10, 96, 100, 384, 1,000, 1,536, 10,000, 100,000 or 1,000,000 trenches.

In one embodiment, devices of this invention may comprise a plurality of units, each unit consisting of one sorter. In one embodiment, devices of this invention comprise an array of unit sorters. In one embodiment, the phrase "a plurality of units" refers to at least two units, or, in another embodiment, more than 5, or, in other embodiments, more than 10, 96, 100, 384, 1,000, 1,536, 10,000, 100,000 or 1,000,000 units. In one embodiment, devices of this invention comprises two sorter units coupled to each other as illustrated in FIGS. 2A, 4A and 4B, FIG. 7 and FIG. 8. According to this embodiment, the two sorter units comprise trenches that span a length that is approximately twice as long as the length of the two shallow regions lengths as exemplified in the figures. This is due to the pillars (e.g. black squares in FIG. 8A) that divide the length of the shallow regions in half, but do not divide or block the length of the trenches.

In one embodiment, the surface of the trenches and/or the shallow regions or the surface of the sorter may be functionalized to reduce or enhance adsorption of species of interest to the surface of the device. In another embodiment, the surface of the trenches and/or shallow region has been functionalized to enhance or reduce the operation efficiency of the device. In one embodiment, the surface of the trenches and/or the surface of the shallow regions or the surface of the sorter may be functionalized to reduce cell adsorption.

Inlets/outlets allow access to the chambers (sorter area or sorter cavity, or sorter trenches area) to which they are connected for the purpose, in one embodiment, of introducing or, in another embodiment, of removing fluids from the sorters or from parts of the microfluidic chip. In one embodiment, inlets allow access to the sorter to which they are connected for the purpose of introducing fluids to the sorter, from a reservoir, or in another embodiment, from a sample stored in a conventional storage means, such as a tube. In another embodiment, the outlet allows access of fluid from the microfluidic sorter according to the methods of this invention. According to this aspect of the invention, the outlet may allow for the removal and storage of the sorted material, or in another embodiment, its conveyance to an analytical module, which in one embodiment, may be coupled thereto. In one embodiment, the inlet and outlet ports may allow for sorter cleaning or sorter sterilizing by conveying a cleaning fluid or a rinsing liquid or gas or a gas mixture or solutions through the sorter before, during or after cell sorting.

3. Methods of this Invention

In one embodiment, methods of this invention use a unique device for the separation of cells based on their deformability. In one embodiment, the barrier for cell passage that is in the core of the separation method is a long slit with a gap size that is less than one dimension or is less than the smallest dimension of a cell. Therefore, in order to squeeze into and through the slit, a cell must deform or change is shape. When a mixture of cells that contains both cells that are capable of deforming and cells that can not deform, is introduced to the device, only the deformable cells may pass through the narrow slits. Other non-deformable cells will slide along the slit, until they exit the device. The cells that pass through the slits may retain their original shape after emerging from the narrow slits on the other side of the slits. Therefore, cells that are separated in this way may be further used or analyzed. As shown in FIG. 8A, deformable cells can thus travel diagonally to the length of the trenches, while non-deformable cells that can not enter the slits, travel straight down and parallel to the trench length. At the bottom of the sorter as shown in FIG. 8, cells will be separated based on their deformability. Deformable cells can be collected at one area at the bottom of the sorter, while non deformable cells can be collected at another area at the bottom of the sorter. The deformable cells travel with the direction of the induced flow. When the flow is induced diagonally to the length of the trenches, the deformable cells may follow this diagonal path. The design of the device and the method causes non-deformable cells to slide along the slits to the outlet, thus preventing excessive accumulation of non-deformable cells at the entrance of the slits, which would have blocked entrance of deformable cells into the slits. Such design allows for continuous smooth sorting of cells.

In one embodiment, this invention provides a method of sorting a fluid mixture comprising a plurality of cells, said method comprising the steps of:
  a) loading a fluid mixture comprising a plurality of cells in a cell sorter comprising:
    i. a first substrate comprising plurality of parallel trenches, arranged at intervals, the trenches each have a contour of a pair of walls and a bottom.
    ii. a second substrate positioned parallel to said first substrate, such that a spacing is formed between said first and said second substrates;
    iii. a sample inlet to said sorter;
    iv. a sample outlet from said sorter;
  b) applying a force field at a non-zero angle with respect to the length of said trenches, whereby applying said force field allows for separation of said plurality of cells; and
  c) collecting separated cells obtained in (b) from said sample outlet.

In one embodiment, the separation is based on the difference in cell deformability of various cells in the fluid mixture. In one embodiment, separation is obtained due to the passage of deformable cells through thin areas between the trenches. In one embodiment, separation is obtained due to the inability of non-deformable cells to pass through the thin regions between the trenches. In one embodiment, separation is obtained by straight or approximately straight flow of non-deformable cells along trenches from an entrance of the sorter to the exit of the sorter, and by diagonal transfer of deformable cells with respect to the trenches length from the entrance of the sorter to the exit of the sorter, through the thin areas.

In one embodiment, the spacing between the first substrate and the second substrate creates thin regions that are arranged at the intervals between the trenches. In one embodiment, the thin regions enable passage of deformable cells and eliminate or reduce the passage of non-deformable cells. In one embodiment, the thin regions provide the separation filter of the device in the method of this invention. In one embodiment, deformable cells that can pass through the thin regions will be collected farther away from the entrance point as compared with non-deformable cells that pass directly (or approximately in a straight line) from the entrance to the outlet of the sorter along the trenches.

In one embodiment, the thin regions are the shallow regions as described herein above. In one embodiment, the thin regions are the filters of the device. In one embodiment, the thin regions are the regions between trenches.

In some embodiments, reagents may be incorporated in the buffers used in the methods and devices of this invention, to enable chemiluminescence detection. In some embodiments the method of detecting the labeled material includes, but is not limited to, optical absorbance, refractive index, fluorescence, phosphorescence, chemiluminescence, electrochemiluminescence, electrochemical detection, voltammetry or conductivity. In some embodiments, detection occurs using laser-induced fluorescence, as is known in the art. In one embodiment, buffers used in this invention comprise the cells to be sorted. In one embodiment, the buffers are or are part of the fluid mixtures used in the invention.

In some embodiments, the labels may include, but are not limited to, fluorescent lanthanide complexes, including those of Europium and Terbium, fluorescein, fluorescamine, rhodamine, tetramethylrhodamine, eosin, erythrosin, coumarin, methyl-coumarins, pyrene, Malacite green, stilbene, Lucifer Yellow, Cascade Blue™, Texas Red, 1,1'-[1,3-propanediylbis[(dimethylimino-3,1-propanediyl]]bis[4-[(3-methyl-2(3H)-benzoxazolylidene)methyl]]-, tetraioide, which is sold under the name YOYO-1, Cy and Alexa dyes, and others described in the 9th Edition of the Molecular Probes Handbook by Richard P. Haugland, hereby expressly incorporated by reference. Labels may be added to 'label' the desired molecules in the cells or the interior or surface of the cells, prior to introduction into the sorters of this invention, in some embodiments, and in some embodiments the label is supplied in a microfluidic chamber. In some embodiments, the labels are attached covalently as is known in the art, or in other embodiments, via non-covalent attachment. In one embodiment, a microfluidic chamber is synonyms with sorters of this invention. In one embodiment, microfluidic chamber comprises sorter(s) of this invention.

In some embodiments, photodiodes, conventional optical microscopes, confocal microscopes, CCD cameras, or photomultiplier tubes maybe used to image the cells and/or the labels thus incorporated, and may, in some embodiments, comprise the apparatus of the invention, representing, in some embodiments, a "lab on a chip" mechanism, as described further, as well, herein below.

In one embodiment, detection is accomplished using laser-induced fluorescence, as known in the art. In some embodiments, the apparatus may further comprise a light source, detector, and other optical components to direct light onto the microfluidic chamber/chip and thereby collect fluorescent radiation thus emitted. The light source may comprise a laser light source, such as, in some embodiments, a laser diode, or in other embodiments, a violet or a red laser diode. In other embodiments, VCSELs, VECSELs, or diode-pumped solid state lasers may be similarly used. In some embodiments, a Brewster's angle laser induced fluorescence detector may used. In some embodiments, one or more beam steering mirrors may be used to direct the beam to a desired location for detection.

In one embodiment, the fluid mixture and/or the buffered solution is flowed through the sorter at a relatively constant flow rate, which in one embodiment ranges from about 0.5-15 μl/minute. According to this aspect of the invention, pressure applied to the device will be such as to accommodate a relatively constant flow rate, as desired, as will be understood by one skilled in the art.

In one embodiment, any of various mechanisms may be employed to manipulate, transport, and/or move fluid within the device, to convey the fluid within the microfluidic sorter, as well as into or out of the sorter. In some embodiments, pressurized fluid flow is applied from a syringe, an automated syringe, a tube, or, in another embodiment, other pressure source, attached to, in one embodiment, an inlet of a device of this invention.

In some embodiments, a pressure stop is positioned between two or more sorters placed in series in an apparatus of this invention, such that the pressure-driven flow through a first sorter does not influence the flow through a second sorter, in some embodiments of this invention. According to this aspect of the invention, and in one embodiment, separation may be affected by the pressure applied for the sorting of the cells within the given sorter.

The sorting devices of this invention are so constructed that passage of cells through the thin regions is size-restricted. An injected main stream of cells separates into different streams based on cell deformability, in some embodiments, as a function of the arrangement of the trenches and thin regions and the applied force fields (electrostatic force field or hydrodynamic force field).

In one embodiment, the force field is applied diagonally to the length of the trenches. The force field may be thus formed, via application of an appropriate stimulus to a reservoir, or to the sorter inlet as described, which is in fluid communication with the trenches, which in turn further convey the stimulus to the trenches of the sorter.

In one embodiment, the electrostatic force field may be applied to the apparatus via the disposition of electrodes on a surface of the apparatus, in conjunction with its their connection to a means of applying voltage, wherein the electrodes are so positioned such that following application of voltage, an electric field is generated, which is diagonal in direction to the length of the trenches in the sorter. In another embodiment, the electrodes are so positioned such that following application of voltage, an electric field is generated, which is diagonal in direction to the length of the trenches of the sorter. In some embodiments, electrodes are formed on the interior or exterior surfaces of the chip and are in electrical communication with the microfluidic channels.

According to this aspect of the invention, and in one embodiment, a power supply is coupled to the electrodes.

In some embodiments of the present invention, a power module is coupled to an external power supply. In other embodiments, the power module is powered using a portable power supply, such as batteries, solar power, wind power, nuclear power, and the like. According to this aspect and in one embodiment, sorters of this invention are portable and can be used in remote areas.

In some embodiments of the present invention, the voltage delivered to the device provides field strength of up to $3.5 \times 10^4$ V/m. In one embodiment, an electric field with strength of at least 100 V/m is applied, or in another embodiment, at least 200 V/m, or in another embodiment, at least 300 V/m.

In one embodiment, the electrode metal contacts can be integrated using standard integrated circuit fabrication technology to be in contact with a reservoir, or in one embodiment, at least one sorter, or in one embodiment, one trench or in another embodiment, a combination thereof, and oriented as such, to establish a directional electric field, as described. Alternating current (AC), direct current (DC), or both types of AC or DC fields can be applied. The electrodes can be made of almost any metal, and in one embodiment, comprise thin Al/Au metal layers deposited on defined line paths. In one embodiment, at least one end of one electrode is in contact with a solution in a reservoir or in the sorter's inlet.

In another embodiment, the sorting device may contain at least two pairs of electrodes, each providing an electric field in a different direction.

In another embodiment, the force field may be a hydrodynamic force field. In another embodiment, the force field may be electrostatic. In one embodiment, the force field is pressure driven. In one embodiment, the pressure is negative and in one embodiment, the pressure is positive.

In one embodiment, a hydrodynamic force field is established via provision of a pressure driven flow, which may originate, in one embodiment, in the reservoirs or in the sample inlet, which convey fluid to the sorter, which in turn convey the fluid to the trenches construction, thus in fact acting as fluidic flow injectors. In one embodiment, the phrases "pressure-driven flow" refers to flow that is driven by a pressure source exerted on the conveyance of fluid through a segment of a channel or a trench and/or a thin region, external to the channel or a trench and/or a thin region segment through which such flow is driven.

Examples of pressure sources include negative and positive pressure sources or pumps external to the channel or sorter segment in question, including electrokinetic pressure pumps, which in one embodiment, are connected to a reservoir, or to the sorter of this invention.

In one embodiment, reference to the term "liquid flow" or "fluid flow" may encompass any or all of the characteristics of flow of fluid or other material through a passage, conduit, channel or across a surface. Such characteristics include without limitation the flow rate, flow volume, the conformation and accompanying dispersion profile of the flowing fluid or other material, as well as other more generalized characteristics of flow, e.g., laminar flow, creeping flow, turbulent flow, etc.

In one embodiment, hybrid flow may comprise pressure-based relay of the liquid sample into the sorter network, followed by electrokinetic movement of materials, or in another embodiment, electrokinetic movement of the liquid followed by pressure-driven flow. It is to be understood that both may be employed in the creation of a force field and may be used in order to affect the sorting efficiency or quality desired, when sorting a mixture of cells or a population of cells.

The sorters of this invention and/or devices comprising the same may be used to sort a fluid mixture comprising a plurality of cells.

In one embodiment, this invention provides a method of sorting a fluid mixture comprising a plurality of cells, said method comprising the steps of:
 a. loading a fluid mixture comprising a plurality of cells in a cell sorter comprising:
  i. a first substrate comprising plurality of parallel trenches, arranged at intervals, the trenches each have a contour of a pair of walls and a bottom.
  ii. a second substrate positioned parallel to said first substrate, such that a spacing is formed between said first and said second substrates;
  iii. a sample inlet to said sorter;
  iv. a sample outlet from said sorter;
 b. applying a force field at a non-zero angle with respect to the length of said trenches, whereby applying said force field allows for separation of said plurality of cells; and
 c. collecting separated cells obtained in (b) from said sample outlet.

In one embodiment, the invention provides an apparatus for quickly and continuously separating cells taking advantage of differential deformability of different cells through periodic arrays of sorters or through single or numerous sorters.

The cells for separation may be any which may be distinguished by the methods and via the devices of this invention.

In one embodiment, cells for separation by methods of this invention include but are not limited to Red blood cells (healthy, glutaraldehyde-treated, heat treated, osmotically swelled or shrunk, malaria-infected, sickle cell anemia, spherocytosis, ellipsocytosis, reticulocytes, older red blood cells (around 120 days)), white blood cells (leukemia, leukostasis, carcinocythemia, and other various types of white blood cells), circulating tumor cells from various organs, cancerous and healthy cells from various organs, bacterial cells, stem cells (e.g. mesenchymal stem cells, hematopoietic stem cells, embryonic stem cells).

In one embodiment, cell sizes range from 1 µm to 100 µm in diameter. In one embodiment cell sizes or cell smallest or largest dimension ranges between 1 µm and 100 µm, between 1 µm and 10 µm, between 1 µm and 5 µm, between 0.5 µm and 10 µm, between 0.5 µm and 3 µm or between 1 µm and 3 µm.

In one embodiment, a solution or buffered medium comprising the cells may be used in the methods and for the devices of this invention. In one embodiment, such solutions or buffered media may further comprise natural or synthetic compounds.

It is to be understood that any complex mixture, comprising two or more cells or two or more cell types which differ in terms of their stiffness or deformability, or combinations thereof, whose separation is desired, may be used for the methods and in the sorters/devices of this invention, and represents an embodiment thereof.

In another embodiment, the solutions or buffered media for use according to the methods and for use in the devices of this invention may comprise any fluid, having cells for separation with the described properties, for example, bodily fluids such as, in some embodiments, blood, urine, serum, lymph, saliva, anal and vaginal secretions, perspiration and semen, or in another embodiment, homogenates of solid tissues, as described, such as, for example, liver, spleen, bone marrow, lung, muscle, nervous system tissue, etc., and may be obtained from virtually any organism, including, for example mammals, rodents, bacteria, etc. In some embodiments, the solutions or buffered media may comprise environmental samples such as, for example, materials obtained from air, agricultural, water or soil sources, which are present in a fluid which can be subjected to the methods of this invention. In another embodiment, such samples may be biological warfare agent samples; research samples and may comprise, for example, glycoproteins, biotoxins, purified proteins, etc.

As will be appreciated by those in the art, virtually any experimental manipulation may have been done on the sample prior to its use in embodiments of the present invention. For example, a variety of manipulations may be performed to generate a liquid sample of sufficient quantity from a raw sample. In some embodiments, gas samples and aerosol samples are so processed to generate a liquid sample containing cells whose separation may be accomplished according to the methods of this invention.

In one embodiment, the device is adapted such that analysis of cells of interest may be conducted, in one embodiment, in the sorter, or in another embodiment, downstream of the sorter. In one embodiment, analysis downstream of the sorter refers to removal of the sorted species from the device, and placement in an appropriate setting for analysis, or in another embodiment, construction of a conduit from the sorter, for example, from a collection port, which relays the sorted material to an appropriate setting for analysis. In one embodiment, such analysis may comprise signal acquisition, and in another embodiment, a data processor. In one embodiment, the signal can be a photon, electrical current/impedance measurement or change in measurements. It is to be understood that the sorting device of this invention may be useful in various analytical systems, including bioanalysis microsystems, due to its simplicity, performance, robustness, and integrability to other separation and detection systems, and any integration of the device into such a system is to be considered as part of this invention.

In one embodiment, the sorters/devices of this invention may be imaged with a two-dimensional detector. Imaging of the sorters/devices or parts thereof, may be accomplished by presenting it to a suitable apparatus for the collection of emitted signals, such as, in some embodiments, optical elements for the collection of light from the sorter.

In another embodiment, the device is coupled to a separation system, or in another embodiment, a detection system, or in another embodiment, an analysis system or in another embodiment, a combination thereof. In another embodiment, the device is coupled to an illumination source and/or an imaging system.

In one embodiment, the sorter may be disposable, and in another embodiment, may be individually packaged, and in another embodiment, have a sample loading capacity of 1-50,000 individual fluid samples. In one embodiment, the sorter can be encased in a suitable housing, such as plastic, to provide a convenient and commercially-ready cartridge or cassette. In one embodiment, the sorter will have suitable features on or in the housing for inserting, guiding, and aligning the device, such that, for example, a sample loading compartment is aligned with a reservoir in another device, which is to be coupled to the sorter. For example, the sorter may be equipped with insertion slots, tracks, or a combination thereof, or other adaptations for automation of the sorting process via a device of this invention.

The sorter may be so adapted, in one embodiment, for high throughput sorting and analysis of multiple samples, such as will be useful in biological applications, as will be appreciated by one skilled in the art.

In one embodiment of the present invention, the sorter is a part of a larger system, which includes an apparatus to excite molecules inside the cells or fluids within the sorter and detect and collect the resulting signals. In one embodiment, a laser beam may be focused upon the device, using a focusing lens, in another embodiment. The generated light signal from the molecules inside the device may be collected by focusing/collection lens, and, in another embodiment, reflected off a dichroic mirror/band pass filter into optical path, which may, in another embodiment, be fed into a CCD (charge coupled device) camera.

In another embodiment, an exciting light source could be passed through a dichroic mirror/band pass filter box and focusing/collecting scheme from the top of the sorter. Various optical components and devices can also be used in the system to detect optical signals, such as digital cameras, PMTs (photomultiplier tubes), and APDs (Avalanche photodiodes).

In another embodiment, the system may further include a data processor. In one embodiment, the data processor can be used to process the signals from a CCD, to a digital image of the separated cells onto a display. In one embodiment, the data processor can also analyze the digital image to provide characterization information, such as quantity and size statistics, histograms, karyotypes, mapping, diagnostics information and display the information in suitable form for data readout.

In one embodiment, subsequent to separation via the methods and utilizing the devices of this invention, further analysis of the sorted cells is possible. Such analysis may be via direct coupling of the machinery necessary for such analysis to the outlet of a sorter, as herein described, or in another embodiment, samples are processed separately.

In one embodiment such subsequent analysis, in addition, or in parallel to those already described, may comprise cell lysis followed by electrophoresis, chromatography, mass spectroscopy, sequencing (for example, for the identification of particular proteins or peptides), NMR and others, as will be appreciated by one skilled in the art.

In some embodiments, features of the present invention include: 1) arrays of alternating trenches and thin areas that serve as the sieving media; 2) A sieving mechanism relying on varied deformability of cells to be separated; 3) various operation methods of the sorter (electrostatic force field based or hydrodynamic force field based, pressure-induced flow mode).

In one embodiment filter is synonyms with the shallow regions and with the thin regions and with narrow gaps and with slits in devices of this invention. In one embodiment, filter is the area in the device through which cells can pass only if they can deform. In one embodiment, filter is the region of the device with at least one dimension smaller than the diameter of a cell or smaller than the smaller or smallest dimension of the cell (e.g. smaller than the cell height in the case of e.g. a red blood cell in one embodiment). In one embodiment, the filter is the region between two parallel trenches and alongside the length of such two trenches. In one embodiment, filters are bordered by pillars. In one embodiment, filters are top covered by the second substrate. In one embodiment, the method can be used on an upside-down turned device, in which case the second substrate is on the bottom and the first substrate is on the top. In one embodiment, the outlet or portions of the outlet of one device can be connected to the inlet of another device to enhance resolution of cell separation. In one embodiment, the outlet of a first device, in the region where the deformable cells or the non-deformable cells are found is connected to the inlet of a second device. In one embodiment, the second device is of the same dimensions as the first device. In one embodiment, the second device has different dimensions. For example and in one embodiment, the second device comprise different thin region depth and/or thin region width and/or different trench length. In one embodiment, the flow speed or other flow characteristics are different in the second device as compared with the first device.

In one embodiment, cells that pass through filters of this invention remain intact after passing through the filter. In one embodiment, passing through the filter does not cause rupture of the cells. In one embodiment, after passage through filters of this invention, cells may re-acquire their original un-deformed shape. In one embodiment, after passing through a filter cells may return to the form that they had before passing through the filters. In one embodiment, the content of the cells is not disturbed by passage through the filters. In one embodiment, the content of the cells is not modified by passage through the filters. In one embodiment, the content of the cells is not being deteriorated by passage through the filters. In one embodiment, the outer surface of the cells is not disturbed/modified and/or deteriorated by cell passage through the filters. In one embodiment, vitality of the cell is not disturbed/modified and/or deteriorated by cell passage through the filters. In another embodiment, cells can remain partially or fully deformed after passage through the filters.

In one embodiment voltage, pressure, timing or a combination thereof are varied, when sorting a sample. In one embodiment, the sample may be repetitively sorted, varying specific conditions with each sort, to further distinguish sorted cells, for example, to obtain greater resolution in terms of stiffness-dependent sorting, as a function of the timing, voltage, pressure, or other means, as will be appreciated by one skilled in the art, in the context of the devices and methods of this invention. In one embodiment, sorted groups of cells can be introduced to the inlet of the same sorter or to the inlet of a subsequent sorter for further sorting in order to achieve further sorting resolution.

In another embodiment, the method further comprises the step of sorting a sample, wherein the pH or ionic strength of the buffered solution is varied at the time of sorting, as described or varied between one sorting cycle and another.

In another embodiment, the method further comprises the step of sorting a sample, wherein the following parameters are modified:

1) Cross-sectional shape (or vertical profile) of the thin/thick regions can be rectangular-shaped to trapezoidal-shaped or triangular-shaped. This is determined by the fabrication process of the filter/trenches matrix.

2) Different regions of the sorter could have different filters and different arrangement of filter arrays. (for example, different thin/thick regions thickness combination along the vertical direction of the sorter).

3) Surface potential (surface charge density) can be changed/modulated by applying external potential to either of the substrates, as a gate potential.

In one embodiment, the methods and/or devices of this invention provide separation capability of cells, such as healthy red blood cells and schizont-stage malaria-infected red blood cells. Artificially stiffened cells (glutaraldehyde-treated) and untreated red blood cells.

In another embodiment, the invention encompasses continuous-flow operation of the sorter ideal for preparatory sample fractionation with increased sample throughput.

In one embodiment, the separation efficiency of the miniature sorter may be comparable to current state of the art cell separation systems such as bump array, as described in Davis, J. A., D. W, Inglis, K. J. Morton, D. A. Lawrence, L. R. Huang, S. Y. Chou, J. C. Sturm and R. H. Austin, "Deterministic hydrodynamics: Taking blood apart" *Proceedings of the National Academy of Sciences of the United States of America* 103, no. 40 (2006): 14779-14784, hereby incorporated herein, in their entirety, by reference. Because of their regular sieving structures, the sorters can be further optimized based on the understanding about the sieving process during the passage of the cells through the nanofilter and/or based on control experiments.

In another embodiment, the Sorter may be batch-fabricated in a cleanroom environment, is chemically and mechanically robust, and can be used over a long period without degradation of its characteristics. The chemical nature of the sorter surface can be tailored for a specific cell population to be analyzed. The Sorter allows the use of different buffer systems, enabling the integration of different cell sensors and separation and reaction chambers in one single chip, without the concern of sieving matrix crosstalk and contamination.

4. Uses of Methods of this Invention

The highlighted features listed above, inter-alia, make the cell sorter an ideal candidate as a cell separation scheme for an integrated sample-preparation microsystem that includes fully integrated multiple separation and purification steps.

In some embodiments, the separation methods/devices/sorters of this invention will include varying voltage or ionic strength of the solutions utilized which in turn may optimize separation of the cells to specific streams, and/or optimization of the resolution or discrete boundaries of each respective stream. This will be apparent to one skilled in the art, and embodiments of such optimization methods are exemplified hereinbelow.

In one embodiment, devices and methods of this invention find applications in clinical research and toxicology, in hematology and in diagnostics. In one embodiment, devices and methods of this invention find applications in forensics, genomics, in pharmaceutical testing and manufacturing, biopharma industry and in drug development. In proteomics, in stem cell research and in cancer cell research and therapeutics.

In one embodiment, devices and methods of this invention find applications in drug delivery and drug screening. In one embodiment, devices and methods of this invention find application in infectious disease treatment.

In one embodiment, devices and methods of this invention find application as part of other or more complex microfluidics systems.

In one embodiment, devices and methods of this invention find applications in the food industry, in environmental devices and methods, in water testing, environmental analysis, in cosmetics, in veterinary products.

In one embodiment, methods of this invention find applications in separating mesenchymal stem cells from hematopoietic stem cells in bone marrow, separating reticulocytes from mature red blood cells for plasmodium vivax cell culture, separating malaria-infected cells from uninfected cells for parasitemia enrichment, separating cancerous cells from healthy cells for analysis, separating older red blood cells from younger red blood cells.

In one embodiment, devices and methods of this invention can be coupled or connected to other biological analysis systems or analytical instruments such as PCR, HPLC, electrophoresis, mass spectrometry, genetic analysis, flow cytometers and cell-manipulation systems. In one embodiment, devices and methods of this invention can be connected to optical imaging systems, optical microscopes, UV/VIS spectrophotometers, devices for single cell manipulation and single cell analysis.

In one embodiment, devices and methods of this invention can be connected to pH meters, electrochemistry meters and/or centrifuges.

In one embodiment, devices and methods of this invention can be coupled to flow cytometry units, immunoassay systems, extraction and/or evaporation instruments.

In one embodiment, devices and methods of this invention can be connected to or may be in itself or maybe part of or may be operated by an automated system, and/or a robot. In on embodiment, devices and methods of this invention can be manufactured as or as part of a rapid test kit, or a LabChip system.

In one embodiment, continuous-flow deformability-based cell sorting device will be the first such device to be able to separate cells continuously based on deformability. This device may make isolation of a sub-population of cells, such as cancer cells, for downstream biochemical or genetic studies easier. Current methods of accomplishing such separations take on the order of 10 seconds per cell. Methods of this invention may be able to accomplish such separations at a rate of 0.01 to 0.1 seconds per cell. Furthermore the design of devices and methods of the present invention will overcome the clogging issues inherent in some of the single-pore studies.

Often in single pore studies, when a rigid cell obstructs the orifice, the device is not able to operate anymore. This invention overcomes that problem by allowing cells that are unable to cross a constricted area to slide along that slit until it exits the device. Therefore, reducing or eliminating clogging of the device. In one embodiment, devices and methods design of this invention may be scaled to filter out the less deformable cells in a living organism and prevent clogging of capillaries. According to this aspect and in one embodiment, devices of this invention maybe implanted in a subject. In one embodiment, devices of this invention may be connected to a subject's blood stream or to other cell populations of the subject through a tube, and used to filter undesired cell sub-populations.

In contrast to previous micro-fabricated devices examining deformability, which exhibit aspect ratios of less than 2:1 the device with repeated slits exhibits an aspect ratio of greater than 10:1. According to this embodiment, aspect ratio is the ratio between the length of a trench and the thin region vertical gap size).

Previous cell separation devices attempt to get cells to pass through small holes, while devices and methods of this invention rely on the principle of transferring the deformable cells through long slits.

In one embodiment, the large aspect ratio that is a characteristic of the slits of the present invention is defined as the width/height with respect to FIG. 2C, where the width<length. With respect to FIG. 8A, the aspect ratio for the shallow region is 100 μm/2.9 μm=34, In FIG. 7, the longer (vertical in image) distance between the pillars (black squares) is 100 μm, and the depth going into the page between the black squares is 2 μm. In that case the aspect ratio is 100 μm/2 μm=50. This difference in geometry when compared with other separation methods more accurately simulates the architecture of the spleen (i.e. tall wooden barrel) and may yield insights into how blood cells deform when they pass through the sinusoidal basement membrane of the spleen.

Current methods of accomplishing such cell separations take on the order of 10 seconds per cell. Devices of the present invention may be able to accomplish such separations at a rate of 0.01 to 0.1 seconds per cell. Furthermore the design of devices of this invention will overcome the clogging issues inherent in some of the single-pore studies. Furthermore, this design may be scaled to filter out the less deformable cells in a living organism and prevent clogging of capillaries.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The following examples are presented in order to more fully illustrate certain embodiments of the invention. They should in no way be construed, however, as limiting the broad scope of the invention.

EXAMPLES

Materials and Methods

The choice of fabrication technology is driven by two requirements. First, fast prototyping is necessary to produce disposable chips with a large number of different designs (i.e. gap depths and angles) outside of a clean room. Second, though polydimethylsiloxane (PDMS) is widely used as a structural material, its low Young's modulus (360-870 kPa) does not allow the fabrication of very low aspect ratio structures and may lead to undesirable bulging of PDMS microchannels under pressure.

In one embodiment, a thiolene based UV-adhesive (Norland Optical Adhesive NOA 81) with a Young's Modulus of 1.4 GPa is chosen for device fabrication. In addition to the Young's modulus value, NOA 81 is transparent and offers better resistance to solvents than PDMS.

First, a 2-level negative PDMS stamp was made using soft lithography techniques from a silicon template. A drop of UV-sensitive prepolymer (NOA 81, Norland Optical Adhesives, USA) was stamped on a glass slide (as backing material) and exposed to UV. Similarly, a drop of NOA was stamped using a flat PDMS slab and exposed to UV on a PDMS backing, which is treated with oxygen plasma to improve adhesion. After peeling off the stamps, the two pieces were brought in contact and bonded by completing the crosslinking with a second exposure to UV.

To eliminate air bubbles while initially filling the device with liquid, the filling solution is placed in vacuum for 30 minutes prior to use. That solution was 3% fetal bovine serum by weight in PBS. This liquid will be pumped into the device for 1 hour prior to experiments to prevent cell adhesion to the device walls during the experiments.

The 2-dimensional separation device consists of a parallel array of slits. Fluid movement was diagonal, so that cells that are less deformable will travel along the entrance of a slit. Cells that are more deformable will travel the direction of fluid movement. In this way, less and more deformable cells will be separated into separate streams that can be collected at the end of the central region. Other mechanical methods of separating cells create local energy minima, which cause less deformable cells to clog and stop the device from working. The method described herein lacks local energy minima, resulting in cells sliding along the slit entrance to the end of the channel.

Example 1

Fabrication of a Microseparator

In one embodiment, to construct a device, the following procedure was used:
1. Holes were punched in a PDMS backing with a biopsy punch, leaving the bores in place.
2. Scotch tape was used to remove dust and contaminants from the PDMS backing.
3. Glass slide was cleaned with tissue paper (such as "kimwipe").
4. Glass slide and the PDMS backing were placed in oxygen plasma (2 minutes vacuum pump, 1 minute oxygen plasma exposure).

5. A drop of NOA was placed on the flat PDMS Slab and another drop on the 2-level PDMS Stamp.
6. The PDMS Backing was pushed on the Flat PDMS Slab, being careful to eliminate any trapped bubbles.
7. The Glass Slide was pushed on the 2-level PDMS stamp being careful to eliminate any trapped bubbles.
8. Both sandwiched components were exposed to a UV DNA gel viewer for 1 minute and 20 seconds.
9. Bores and NOA 81 were removed from the PDMS Backing.
10. The pieces from the 2-level PDMS Stamp and the Flat PDMS Slab were delaminated.
11. The delaminated pieces were bonded together.
12. The bonded device was exposed to the UV DNA gel viewer for 15 minutes.
13. The device was wrapped in aluminum foil and was placed in an oven at 65 degrees C. (Celsius) overnight.

Example 2

Operation of the Sorter

With reference to FIG. 4A, a solution of PBS 1× and 0.2% w/v Pluronic F108 (a surfactant) and Bovine Serum Albumin 1% w/v (another surfactant) was prepared. The device was filled with this solution by applying pressure to one of the reservoirs. 1 µL of whole blood was mixed with 100 µL of this solution. The mixture was injected into the entrance reservoir of the device shown by using a syringe. The pressure difference between the two reservoirs was 40 kPa and was generated by using a pressure regulator. The cell concentration was approximately 0.5% hematocrit. Mobility was measured by tracking individual cells over a distance of 100 µm.

Example 3

Operation of the Microseparator

With reference to FIG. 6, the solution used in this device is the same as that used in example 2. To create the Glutaraldehyde-treated cells, 1 µL of whole blood was mixed in 0.003% Glutaraldehyde in PBS 1× and allowed to sit for 30 minutes. The cells were then washed 3 times with the PBS-Pluronic-BSA solution. The pressure difference across the reservoirs was 1 atmospheres vertically and 1 atmospheres horizontally. 100 cells were measured for each population at a displacement of 550 µm from the injection point. The shallow region of the device was 2.1 µm and the deep region of the device was 8.8 µm. 20 sorting units were in the device array, with a period between units of 20 µm. The operation temperature was room temperature, 23° C. Locations were measured as cells passed 550 µm from the point of injection.

Example 4

Separation of Red Blood Cells

With reference to FIG. 7, the solution used in this device and the procedure used to prepare the cells is the same as that used in example 2. The pressure difference across the reservoirs was 1 atmospheres vertically and 0.5 atmospheres horizontally using syringes. The shallow region of the device was 1.6 µm, and the deep region of the device was 14.4 µm. Two cells are displayed. The cells were not dyed in any way. 4 sorting units are displayed. The operation temperature was room temperature, 23° C.

Example 6

Infected vs. Normal Red Blood Cells

With reference to FIG. 9, the distance between the second substrate (cover) and the top of the trenches is 2.9 µm. The distance between the second substrate (cover) and the bottom of the trenches is 8.8 µm. The buffer solution (PBS-Pluronic-BSA) solution used is the same as that in Example 2. 1 uL of cells were diluted in the PBS-Pluronic-BSA solution and 1 uL of Hoechst dye was added. The Hoechst dye dyes DNA, and only the schizont-stage infected red blood cells have DNA inside. Therefore, they fluoresce, while the uninfected cells appear as black shadows. The vertical pressure was 1 atmosphere and the horizontal pressure was also 1 atmosphere. 64 trenches were in the device. Locations were measured by tracking the fluorescent and shadows.

What is claimed is:

1. A method of sorting a fluid mixture comprising a plurality of cells, said method comprising the steps of:
    a) loading the fluid mixture comprising a plurality of deformable and non-deformable cells in a microfluidic cell sorter comprising:
        i. a first substrate comprising plurality of parallel trenches, arranged at intervals, the trenches each have a contour of a pair of walls and a bottom;
        ii. a second substrate positioned parallel to said first substrate, such that a spacing is formed in the form of a plurality of shallow regions or slits between said first and said second substrates to allow deformable cells to pass through one trench to another, and wherein a supporting structure holds said second substrate suspended over said first substrate;
        iii. a sample inlet to said sorter;
        iv. a sample outlet from said sorter;
    b) applying a force field diagonally with respect to the length of said trenches, whereby applying said force field allows diagonal fluid flow with respect to the shallow regions or slits for separation of said plurality of cells, wherein said deformable cells deform while crossing from one trench to another through said shallow regions or slits, and said non-deformable cells slide along said shallow regions or slits in a direction parallel to said trenches resulting in a continuous sorting of said deformable and non-deformable cells, and ensuring that said spacing is smaller than the smallest dimension of the cells; and
    c) collecting separated cells obtained in (b) from said sample outlet.

2. The method of claim 1, wherein said separation is a result of the difference in cell deformability of different cells in said plurality of cells.

3. The method of claim 1, wherein said separation is a result of the difference in cell stiffness of different cells in said plurality of cells.

4. The method of claim 1, wherein a sub-population of cells is isolated.

5. The method of claim 4, wherein said sub-population of cells are cancer cells.

6. The method of claim 1, wherein cell separation rate is less than 0.1 seconds per cell.

7. The method of claim 1, wherein cell separation rate ranges between 0.1-1 seconds per cell.

8. The method of claim 1, wherein said method reduces or eliminates clogging of said sorter.

9. The method of claim 1, wherein said diagonal force field applied with respect to the length of said trenches is an electrostatic force field.

10. The method of claim 9, wherein said electrostatic force field provides an electroosmotic driving force for said fluid.

11. The method of claim 1, wherein said fluid has an ionic strength of about 1-1000 mM.

12. The method of claim 1, wherein said sorting is deformability-based.

13. The method of claim 1, wherein said sorting is size-based.

14. The method of claim 1, wherein said sorting is charge-based.

15. The method of claim 1, wherein the depth of said trenches ranges between 10-10,000 nm.

16. The method of claim 1, wherein the spacing between said second substrate and said first substrate ranges between 10-5000 nm.

17. The method of claim 1, wherein the width of said trenches ranges between 10-100,000 nm.

18. The method of claim 1, wherein the length of said trenches ranges between 10 nm and 1000 μm.

19. The method of claim 1, wherein said sample inlet, said sample outlet or a combination thereof are in fluid communication with a reservoir.

20. The method of claim 19, wherein voltage is applied to said reservoir.

21. The method of claim 20, wherein said applied voltage is less than 1000 V.

22. The method of claim 20, wherein pressure is applied to said reservoir.

23. The method of claim 1, wherein said fluid mixture comprises a cell mixture having more than one type of cells.

24. The method of claim 1, wherein said fluid mixture comprises a buffered solution.

25. The method of claim 1, further comprising the step of sorting a sample of said fluid mixture two or more times, wherein the pH or ionic strength of said buffered solution is varied at the time of said sorting.

26. The method of claim 1, wherein said trenches comprise a material having a Young's Modulus of at least 500 kPa.

27. The method of claim 1, wherein the ratio between length of said trenches and the spacing between the first and second substrates is at least 3:1.

28. The method of claim 1, wherein the ratio between length of said trenches and the spacing between the first and second substrates ranges between 10:1 and 100:1.

29. The method of claim 1, wherein the spacing between said second substrate and said first substrate is less than 50% of the spacing between the second substrate and the bottom of said trenches of said first substrate.

30. The method of claim 1, wherein the spacing between said second substrate and said first substrate ranges between 10% and 70% of the spacing between the second substrate and the bottom of said trenches of said first substrate.

31. The method of claim 1, wherein said spacing between said first and said second substrate ranges between 0.1-10 μm.

32. The method of claim 1, wherein said force field is an electric field.

33. The method of claim 1, wherein said sample inlet comprises sample loading ports.

34. The method of claim 1, wherein said sample outlet comprises sample collection ports.

35. The method of claim 1, wherein said first substrate, said second substrate, portions thereof or a combination thereof comprises polydimethylsiloxane, polyurethane, glass, silicon, $SiO_2$ or a combination thereof.

36. The method of claim 1, wherein said first substrate, said second substrate, portions thereof or a combination thereof comprises a transparent material.

37. The method of claim 1, wherein the surface of said first substrate, said second substrate, portions thereof or a combination thereof are coated to reduce cell adhesion.

38. The method of claim 1, wherein said sorter is part of a microchip.

39. The method of claim 38, wherein said microchip is disposable.

* * * * *